United States Patent [19]

Allais et al.

[11] 4,105,777

[45] Aug. 8, 1978

[54] INDOLES

[75] Inventors: André Allais, Gagny; Jean Meier, La Varenne Saint-Hilaire; Roger Deraedt, Pavillons-sous-Bois, all of France

[73] Assignee: Roussel Uclaf, Paris, France

[21] Appl. No.: 758,633

[22] Filed: Jan. 12, 1977

[30] Foreign Application Priority Data

Jan. 21, 1976 [FR] France .................. 76 01560
Oct. 1, 1976 [FR] France .................. 76 29652

[51] Int. Cl.² ............... A61K 31/40; C07D 209/20
[52] U.S. Cl. ....................... 424/274; 260/326.14 R
[58] Field of Search ............... 260/326.14 R; 424/274

[56] References Cited

U.S. PATENT DOCUMENTS 3,047,584  7/1962  Elkin .................. 260/326.14 R X
3,557,142  1/1971  Bell ..................... 260/326.13

FOREIGN PATENT DOCUMENTS 888,535  1/1962  United Kingdom ........... 260/326.14 R

OTHER PUBLICATIONS

Chem. Abstracts, 83: 131402w.

*Primary Examiner*—Ethel G. Love
*Attorney, Agent, or Firm*—Hammond & Littell

[57] ABSTRACT

Indoles of the formula

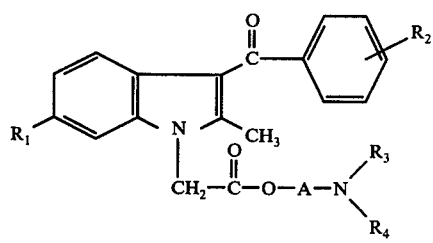

wherein $R_1$ is selected from the group consisting of hydrogen, halogen, —$CF_3$, alkyl of 1 to 8 carbon atoms and alkoxy of 1 to 8 carbon atoms, $R_2$ is in the 2,3 or 4 position and is selected from the group consisting of halogen, —$CF_3$ and alkyl, alkoxy and alkylthio of 1 to 8 carbon atoms, A is selected from the group consisting of branched alkylene of 3 to 5 carbon atoms and —$(CH_2)_n$— and $n$ is a number of 2 to 5 and $R_3$ and $R_4$ are alkyl of 1 to 8 carbon atoms or taken together with the nitrogen atom form a heterocyclic ring selected from the group consisting of piperidinyl, pyrrolidinyl, morpholinyl, piperazinyl and N-alkyl piperazinyl with 1 to 4 alkyl carbon atoms and their non-toxic, pharmaceutically acceptable acid addition salts having analgesic activity and their preparation.

19 Claims, No Drawings

INDOLES

STATE OF THE ART

U.S. Pat. No. 3,856,967 and French Pat. No. 2,002,284 and No. 2,280,379 describe 1-carboxyalkyl-2-methylindoles having analgesic and anti-inflammatory activity.

OBJECTS OF THE INVENTION

It is an object of the invention to provide the novel indoles of formula I and their non-toxic, pharmaceutically acceptable acid addition salts and a novel process for their preparation.

It is another object of the invention to provide novel analgesic compositions and a novel method of relieving pain in warm-blooded animals, including humans.

These and other objects and advantages of the invention will become obvious from the following detailed description.

THE INVENTION

The novel products of the invention are selected from the group consisting of indoles of the formula

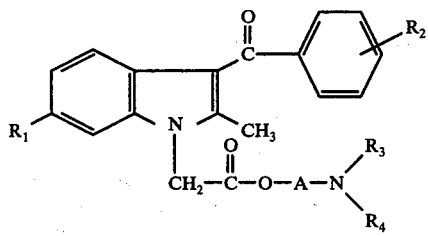

wherein $R_1$ is selected from the group consisting of hydrogen, halogen, —$CF_3$, alkyl of 1 to 8 carbon atoms and alkoxy of 1 to 8 carbon atoms, $R_2$ is in the 2,3 or 4 position and is selected from the group consisting of halogen, —$CF_3$ and alkyl, alkoxy, and alkylthio of 1 to 8 carbon atoms, A is selected from the group consisting of branched alkylene of 3 to 5 carbon atoms and —$(CH_2)_n$— and n is a number of 2 to 5 and $R_3$ and $R_4$ are alkyl of 1 and 8 carbon atoms or taken together with the nitrogen atom form a heterocyclic ring selected from the group consisting of piperidinyl, pyrrolindinyl, morpholinyl, piperazinyl and N-alkyl piperazinyl with 1 to 4 alkyl carbon atoms and their non-toxic, pharmaceutically acceptable acid addition salts.

When $R_1$ or $R_2$ are halogen, they are preferably chlorine, bromine or fluorine. Examples of $R_1$, $R_2$, $R_3$ or $R_4$ as alkyl are methyl, ethyl, n-propyl, or n-butyl. Examples of $R_1$ and $R_2$ as alkoxy are methoxy, ethoxy, n-propoxy and n-butoxy. When A is linear alkylene, n is peferably 2, 3 or 4 and when A is branched alkylene, A is preferably isopropyl.

Examples of suitable acids for the formation of the acid addition salts are mineral acids such as hydrochloric acid, hydrobromic acid, sulfuric acid or phosphoric acid or organic acids such as acetic acid, formic acid, oxalic acid, etc and sulfonic acids such as methane sulfonic acid, or p-toluene sulfonic acid.

Among the preferred compounds of formula I are those where $R_1$ is methoxy, ethyl or hydrogen, those wherein n is 2 or 3, those where $R_2$ is methoxy, chlorine, fluorine or —$CF_3$, those wherein $R_3$ and $R_4$ are alkyl, especially methyl or ethyl, those wherein $R_3$ and $R_4$ together with the nitrogen atom form pyrrolindinyl or morpholinyl and those wherein A is isopropyl and, of course, their acid addition salts, preferably their hydrochloride.

The most preferred compound is 2-(dimethylamino)-ethyl-2-methyl-6-methoxy-benzoyl) [1H] indole-1-acetate and its non-toxic, pharmaceutically acceptable acid addition salts.

The novel process of the invention for the preparation of the compounds of formula I comprises reacting a compound of the formula

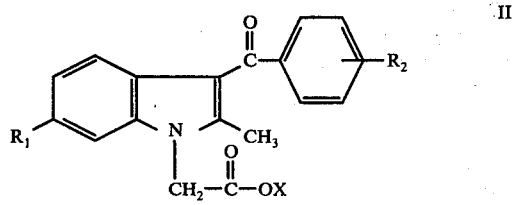

wherein $R_1$ and $R_2$ have the above definition and X is alkyl of to 8 carbon atoms with a compound of the formula

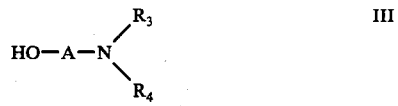

wherein A, $R_3$ and $R_4$ have the above definition to form the compound of formula I which may be salified with an acid, if desired.

The said reaction is preferably effected in an organic solvent at 50° to 200° C and in the presence of an alkaline agent such as an alkali metal hydride, amide or alcoholate. X is preferably methyl, ethyl, n-propyl or n-butyl. The compounds of formula II may be prepared by the process of Belgium Pat. No. 726,610.

The novel analgesic compositions of the invention are comprised of an analgesically effective amount of at least one compound of formula I and its non-toxic, pharmaceutically acceptable acid addition salts and an inert phamaceutical carrier. The compositions may be in the form of tablets, dragees, gelules, granules, suppositories, injectable solutions or suspensions, pomades, creams, gels and aerosol preparations prepared in the usual manner. Particularly preferred is 2-(dimethylamino)-ethyl-2-methyl-6-methoxy-3-(4-methoxybenzoyl) [1H] indole-1acetate and its salts especially its hydrochloride.

Examples of suitable excipients or carriers are talc, arabic gum, lactose, starch, magnesium stearate, cacao butter, aqueous or non-aqueous vehicles, fatty bodies of animal or vegetable origin, paraffinic derivatives, glycols, preservations and diverse wetting agents, dispersants and emulsifiers.

The compositions due to their analgesic activity are useful for the treatment of muscular, articular of nervous pains, dental pains and migraines.

The novel method of the invention for relieving pain in warm-blooded animals, including humans, comprises administering to warm-blooded animals an analgesically effective amount of at least one compound of formula I and its non-toxic, pharmaceutically acceptable acid addition salts. The compounds may be administered orally, rectally, parenterally, or locally by topical application to the skin or mucous. The usual useful dose is 0.4 to 40 mg/kg depending upon the method of administration and the specific compound.

In the following examples there are described several preferred embodiments to illustrate the invention. However, it is to be understood that the invention is not to be limited to the specific embodiments.

EXAMPLE 1

2-(dimethylamino)-ethyl-2-methyl-6-methoxy-3-(4-methoxybenzoyl) [1] indole-1-acetate hydrochloride 7.5 g of methyl 2-methyl-6-methoxy-3-(4-methoxybenzoyl) [1H] indole-1-acetate were added with stirring under a nitrogen current to a mixture of 50 ml of dimethylamino ethanol and 50 ml of anhydrous toluene and the mixture was heated to distill the toluene and was then cooled to 50° C. 150 mg of a 50% suspension of sodium hydride in oil were added thereto and the reaction mixture was heated to 100° C for 4 hours. The mixture was cooled to 20° C and 100 ml of methylene chloride were added. The mixture was washed with water and was decanted and the aqueous phase was extracted with methylene chloride. The organic phase was washed with water, dried and evaporated to dryness to obtain 6.33 g of product. The latter was dissolved in 15 ml of ethanol and 3.05 ml of 5.17N anhydrous hydrochloric acid in ethanol were added thereto. The mixture was cooled on an ice bath and was vacuum filtered. The crystals recovered were washed with ethanol and dried to obtain 5.47 g of product. The latter was crystallized to obtain 4.985 g of the hydrochloride of 2-(dimethylamino)-ethyl 2-methyl-6-methoxy-3-(4-methoxybenzoyl) [1H] indole-1-acetate melting at 197-8° C.

EXAMPLE 2

Using the procedure of Example 1, methyl 2-methyl-6-methoxy-3-(4-chlorobenzoyl) [1H] indole-1-acetate was reacted with dimethylamino ethanol to obtain the hydrochloride of 2-(dimethylamino)-ethyl 2-methyl-6-methoxy-3-(4-chlorobenzoyl) [1H] indole-1-acetate melting at 197° C.

EXAMPLE 3

Using the procedure of Example 1, methyl 2-methyl-6-methoxy-3-(4-chlorobenzoyl) [1H] indole-1-acetate was reacted with diethylamino ethanol to obtain the hydrochloride of 2-(diethylamino)-ethyl 2-methyl-6-methoxy-3-(4-chlorobenzoyl) [1H] indole-1-acetate melting at 167°–171° C.

EXAMPLE 4

Using the procedure of Example 1, methyl 2-methyl-6-methoxy-3-(4-chlorobenzoyl) [1H] indole-1-acetate was reacted with pyrrolidinyl ethanol to obtain the hydrochloride of 2-(pyrrolidinyl)-ethyl 2-methyl-6-methoxy-3-(4-chlorobenzoyl) [1H] indole-1-acetate melting at 156° C.

EXAMPLE 5

2-(dimethylamino)-ethyl 2-methyl-6-methoxy-3-(4-trifluoromethyl-benzoyl) [1H] indole-1-acetate hydrochloride A mixture of 4.2 g of methyl 2-methyl-6-methoxy-3-(4-trifluoromethyl-benzoyl) [1H] indole-1-acetate, 3.7 ml of dimethylamino ethanol and 100 ml of toluene was refluxed for an hour while recycling the toluene after passage through a column filled with siliporite and after the addition of 50 mg of a 50% oily suspension of sodium hydride were added thereto, the mixture was refluxed for 3 hours. The mixture was cooled and evaporated to dryness and the residue was taken up in anhydrous ether. The mixture was filtered and the insolubles were added again to anhydrous ether. An ethanolic solution of hydrochloric acid was added and the mixture was stirred for 4 hours and was vacuum filtered. The recovered crystals were washed with ether to obtain 4.8 g of the hydrochloride of 2-(dimethylamino)-ethyl 2-methyl-6-methoxy-3-(4-trifluoromethyl benzoyl) [1H] indole-1-acetate melting at 170° C.

EXAMPLE 6

Using the procedure of Example 5, methyl 2-methyl-6-methoxy-3-(4-methoxybenzoyl) [1H] indole-1-acetate was reacted with diethylamino ethanol to obtain the hydrochloride of 2-(diethylamino) ethyl 2-methyl-6-methoxy-3-(4-methoxybenzoyl) [1H] indole-1-acetate melting at 134° C.

EXAMPLE 7

Using the procedure of Example 5, methyl 2-methyl-6-methoxy-3-(4-methoxybenzoyl) [1H] indole-1-acetate was reacted with 3-dimethylamino-2-propanol to obtain the hydrochloride of 3-(dimethylamino)-2-propyl 2-methyl-6 -methoxy-3-(4-methoxybenzoyl) [1H] indole-1-acetate melting at 130°≃135° C.

EXAMPLE 8

Using the procedure of Example 5, methyl 2-methyl-6-methoxy-3-(4-methoxybenzoyl) [1H] indole-1-acetate was reacted with 1-(pyrrolidinyl)-ethanol to obtain the hydrochloride of 2-(1-pyrrolidinyl)-ethyl 2-methyl-6-methoxy-3-(4-methoxybenzoyl) [1H] indole-1-acetate melting at 182° C.

EXAMPLE 9

Using the procedure of Example 5, methyl 2-methyl-6-methoxy-3-(4-methoxybenzoyl) [1H] indole-1-acetate was reacted with 3-dimethylamino-propanol to obtain the hydrochloride of 3-(dimethylamino)-propyl 2-methyl-6-methoxy-3-(4-methoxybenzoyl) [1H] indole-1-acetate melting at 125° C.

EXAMPLE 10

Using the procedure of Example 5, methyl 2-methyl-6-methoxy-3-(4-fluorobenzoyl) [1H] indole-1-acetate was reacted with dimethylamino-ethanol to obtain the hydrochloride of 2-(dimethylamino)-ethyl 2-methyl-6-methoxy-3-(4-fluorobenzoyl) [1H] indole-1-acetate melting at 200° C.

EXAMPLE 11

Using the procedure of Example 5, methyl 2-methyl-3-(4-chlorobenzoyl) [1H] indole-1-acetate was reacted with dimethylamino-ethanol to obtain the hydrochloride of 2-(dimethylamino)-ethyl 2-methyl-3-(4-chlorobenzoyl) [1H] indole-1-acetate melting at 164° C.

EXAMPLE 12

Using the procedure of Example 5, methyl 2-methyl-6-methoxy-3-(4-methoxybenzoyl) [1H] indole-1-acetate was reacted with 4-(morpholinyl) ethanol to obtain the hydrochloride of 2-/4-(morpholinyl)/-ethyl 2-methyl-6-methoxy-3-(4-methoxybenzoyl) [1H] indole-1-acetate melting at 162° C.

EXAMPLE 13

Using the procedure of Example 5, methyl 2-methyl-6-ethyl-3-(4-chlorobenzoyl) [1H] indole-1-acetate was reacted with dimethylamino ethanol to obtain the hydrochloride of 2-(dimethylamino)-ethyl 2-methyl-6-ethyl-3-(4-chlorobenzoyl) [1H] indole-1-acetate melting at 200° C.

EXAMPLE 14

Tablets were prepared with 20 mg of the product of Example 1 with sufficient excipient of lactose, starch, talc and magnesium stearate for a final weight of 200 mg and 50 mg of the product of Example 5 with sufficient excipient of talc, lactose, starch and magnesium stearate to obtain a final weight of 350 mg.

PHARMACOLOGICAL DATA

A. Analgesic Activity

The test employed was that of Koster et al [Fed. Proc. Vol. 18 (1959), p. 412] in which an intraperitoneal injection of acetic acid to mice provokes repeated stretching and twisting movements which persists for more than 6 hours. Analgesics prevent or diminish this syndrome which is considered as the exterioriazation of diffuse abdominal pain. The animals received a 1% solution of acetic acid in water and the dose releasing the syndrome under these conditions was 0.01 ml/g or 100 mg/kg of acetic acid. The test product was orally administered a half hour before the acetic acid injection and the mice were starved for 24 hours before the test. The stretchings were observed and counted for each mouse for a period of 15 minutes beginning after the acetic acid injection. The results were expressed as the $DA_{50}$ which is the dose which reduced by 50% the number of stretchings as compared to the control animals. The results are reported in Table I.

TABLE I

| Compound of Example | $DA_{50}$ in mg/kg |
| --- | --- |
| 1 | 1 |
| 2 | 6 |
| 3 | 3.5 |
| 4 | 10 |
| 5 | 10 |
| 6 | 10 |
| 10 | 7 |
| 11 | 4 |
| 13 | 4 |

Various modifications of the products and processes of the invention may be made without departing from the spirit or scope thereof and it should be understood that the invention is to be limited only as defined in the appended claims.

We claim:

1. A compound selected from the group consisting of indoles of the formula

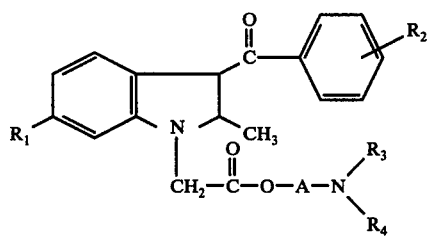

wherein $R_1$ is selected from the group consisting of hydrogen, halogen, —$CF_3$, alkyl of 1 to 8 carbon atoms and alkoxy of 1 to 8 carbon atoms, $R_2$ is in the 2, 3 or 4 position and is selected from the group consisting of halogen, —$CF_3$ and alkyl, alkoxy and alkylthio of 1 to 8 carbon atoms, A is selected from the group consisting of branched alkylene of 3 to 5 carbon atoms and —$(CH_2)_n$— and $n$ is a number of 2 to 5 and $R_3$ and $R_4$ are alkyl of 1 to 8 carbon atoms and their non-toxic, pharmaceutically acceptable acid additions salts.

2. A compound of claim 1 wherein $R_1$ is methoxy.

3. A compound of claim 1 wherein $n$ is 2.

4. A compound of claim 1 wherein $R_2$ is methoxy or chloro.

5. A compound of claim 1 wherein $R_3$ and $R_4$ are alkyl of 1 to 8 carbon atoms.

6. A compound of claim 5 wherein $R_3$ and $R_4$ are methyl or ethyl.

7. A compound of claim 1 selected from the group consisting of 2-(dimethylamino)-ethyl 2-methyl-6-methoxy-3-(4-methoxybenzoyl) [1H] indole-1-acetate and its non-toxic, pharmaceutically acceptable acid addition salts.

8. A compound of claim 1 selected from the group consisting of 2-(dimethylamino)-ethyl 2-methyl-6-methoxy-3-(4-chlorobenzoyl) [1H] indole-1-acetate and its non-toxic, pharmaceutically acceptable acid addition salts.

9. A compound of claim 1 selected from the group consisting of 2-(diethylamino)-ethyl 2-methyl-6-methoxy-3-(4-chlorobenzoyl) [1H] indole-1-acetate and its non-toxic, pharmaceutically acceptable acid addition salts.

10. A compound of claim 1 selected from the group consisting of 2-(dimethylamino)-ethyl 2-methyl-6-methoxy-3-(4-trifluoromethylbenzoyl) [1H] indole-1-acetate and its non-toxic, pharmaceutically acceptable acid addition salts.

11. A compound of claim 1 selected from the group consisting of 2-(diethylamino)-ethyl 2-methyl-6-methoxy-3-(4-methoxybenzoyl) [1H] indole-1-acetate and its non-toxic, pharmaceutically acceptable acid addition salts.

12. A compound of claim 1 selected from the group consisting of 2-(dimethylamino)-ethyl 2-methyl-6-methoxy-3-(4-fluorobenzoyl) [1H] indole-1-acetate and its non-toxic, pharmaceutically acceptable acid addition salts.

13. A compound of claim 1 selected from the group consisting of 2-(dimethylamino)-ethyl 2-methyl-3-(4-chlorobenzoyl) [1H] idole-1-acetate and its non-toxic, pharmaceutically acceptable acid addition salts.

14. A compound of claim 1 selected from the group consisting of 2-(dimethylamino)-ethyl 2-methyl-6-ethyl-3-(4-chlorobenzoyl) [1H] indole-1-acetate and its non-toxic, pharmaceutically acceptable acid addition salts.

15. A compound of claim 1 in the form of its hydrochloride salt.

16. An analgesic composition comprising an analgesically effective amount of at least one compound of claim 1 and an inert pharmaceutical carrier.

17. A composition of claim 16 wherein the compound is 2-(dimethylamino) ethyl 2-methyl-6-methoxy-3-(4-methoxybenzoyl) [1H] indole-1-acetate or its hydrochloride.

18. A method of relieving pain in warm-blooded animals comprising administering to warm-blooded animals an analgesically effective amount of at least one compound of claim 1.

19. The method of claim 18 wherein the compound is 2-(dimethylamino)-ethyl 2-methyl-6-methoxy-3-(4-methoxybenzoyl) [1H] indole-1-acetate or its hydrochloride.

* * * * *